(12) United States Patent
Campbell

(10) Patent No.: US 11,147,912 B1
(45) Date of Patent: Oct. 19, 2021

(54) IV ORGANIZER

(71) Applicant: Flo Medical, LLC, Eagle Mountain, UT (US)

(72) Inventor: Sean Campbell, Eagle Mountain, UT (US)

(73) Assignee: Flo Medical, LLC, Eagle Mountain, UT (US)

( * ) Notice: Subject to any disclaimer, the term of this patent is extended or adjusted under 35 U.S.C. 154(b) by 0 days.

(21) Appl. No.: 16/697,757

(22) Filed: Nov. 27, 2019

(51) Int. Cl.
*A61M 5/14* (2006.01)
*C08L 23/12* (2006.01)

(52) U.S. Cl.
CPC ........ *A61M 5/1418* (2013.01); *A61M 5/1415* (2013.01); *C08L 23/12* (2013.01); *A61M 2209/082* (2013.01); *A61M 2209/084* (2013.01)

(58) Field of Classification Search
CPC .............. A61M 5/1418; A61M 5/1415; A61M 2209/082; A61M 2209/084; A61M 5/1417
See application file for complete search history.

(56) References Cited

U.S. PATENT DOCUMENTS

| | | | | |
|---|---|---|---|---|
| 851,720 A * | 4/1907 | Williamson | ........ | E04D 13/1407 52/219 |
| 973,777 A * | 10/1910 | Grissom | ............. | E04D 13/1407 52/219 |
| 1,127,844 A * | 2/1915 | Anderson | ........... | E04D 13/1407 52/219 |
| 1,294,951 A * | 2/1919 | Rohrbacher | ........... | B65D 63/04 24/20 EE |
| 1,342,918 A * | 6/1920 | Legg | ........................ | F23J 13/00 285/42 |
| 1,669,446 A * | 5/1928 | Bowers | ..................... | F16L 3/14 248/59 |
| 1,690,643 A * | 11/1928 | Lavender | ............... | F16L 33/035 24/20 R |
| 2,249,764 A * | 7/1941 | Hothersall | ............. | B65D 63/04 24/20 R |
| 2,648,326 A * | 8/1953 | Epstein | .................... | F23J 13/04 126/317 |
| 2,648,511 A * | 8/1953 | Epstein | ..................... | F16L 3/00 248/57 |
| 2,908,061 A * | 10/1959 | Adams | ..................... | F16L 33/04 24/279 |
| 2,965,342 A * | 12/1960 | Goldstone | ................. | F16L 3/00 248/57 |
| 3,004,740 A * | 10/1961 | Lane | ........................ | F23J 13/00 248/57 |
| 3,602,468 A * | 8/1971 | Stone | ........................ | F16L 3/00 248/57 |
| 3,750,241 A * | 8/1973 | Bootha | .................... | F16L 33/04 24/279 |

(Continued)

*Primary Examiner* — Christopher Garft
(74) *Attorney, Agent, or Firm* — Thorpe, North & Western, LLP

(57) ABSTRACT

An IV organizer is presented to selectively receive intravenous tubing. The IV organizer has a flat plate with tubing clamps on one face, and rails on the opposite face aligned with the tubing clamps. The tubing clamps comprise flexible fingers to receiving the IV tubing. The tubing clamps are positioned and oriented to position and orient the IV tubing in an organized manner. The IV organizer is formed of material comprising polypropylene and recycled material from previously used IV organizers.

20 Claims, 3 Drawing Sheets

(56) References Cited

U.S. PATENT DOCUMENTS

| | | | | |
|---|---|---|---|---|
| 3,809,350 | A * | 5/1974 | Lane | F16L 5/00 248/57 |
| 4,106,197 | A * | 8/1978 | Russell | A47J 43/282 30/324 |
| D257,947 | S * | 1/1981 | Reynoso | 248/57 |
| 4,318,234 | A * | 3/1982 | Charles | B41M 5/165 40/665 |
| 4,944,683 | A * | 7/1990 | Leonardo | H01R 4/643 24/279 |
| 5,020,748 | A * | 6/1991 | Okajima | B60K 37/04 248/27.1 |
| 5,172,879 | A * | 12/1992 | Calmettes | F16L 3/1233 24/23 EE |
| 5,275,601 | A * | 1/1994 | Gogolewski | A61B 17/8052 411/399 |
| 5,478,033 | A * | 12/1995 | Hungerford, Jr. | F16L 3/08 248/74.3 |
| 5,522,571 | A * | 6/1996 | Simmons | F16L 3/14 248/59 |
| 5,581,924 | A * | 12/1996 | Peterson | G09F 3/005 40/633 |
| 5,697,585 | A * | 12/1997 | Hungerford, Jr. | F16L 3/08 248/74.3 |
| 5,730,608 | A * | 3/1998 | Legrady | H01R 12/57 439/78 |
| 5,746,401 | A * | 5/1998 | Condon | F16L 3/133 248/62 |
| 6,557,805 | B1 * | 5/2003 | Snyder | F16L 3/137 248/60 |
| 6,581,885 | B2 * | 6/2003 | Polad | F16L 3/137 24/16 PB |
| 6,685,153 | B2 * | 2/2004 | Foreman | F16L 3/14 24/16 PB |
| 7,083,151 | B2 * | 8/2006 | Rapp | F16L 3/133 24/16 PB |
| 7,240,446 | B2 * | 7/2007 | Bekker | G09F 3/005 40/633 |
| 7,487,791 | B1 | 2/2009 | Bradley | |
| 7,490,600 | B2 * | 2/2009 | Kopp | F23J 13/00 126/307 R |
| 7,559,512 | B1 * | 7/2009 | diGirolamo | F16L 3/1233 24/23 R |
| 7,658,027 | B2 * | 2/2010 | Jain | B42D 15/00 40/633 |
| 7,784,209 | B2 * | 8/2010 | Greer | G09F 3/005 40/633 |
| 8,974,421 | B1 | 3/2015 | Khalaj | |
| 8,975,519 | B2 * | 3/2015 | Lalancette | H05K 5/0204 174/58 |
| 2004/0127899 | A1 * | 7/2004 | Konieczynski | A61B 17/7059 606/281 |
| 2004/0173232 | A1 * | 9/2004 | Chang | A45D 31/00 132/73 |
| 2005/0273105 | A1 * | 12/2005 | Konieczynski | A61B 17/8047 606/289 |
| 2006/0230661 | A1 * | 10/2006 | Bekker | G09F 3/005 40/633 |
| 2007/0215140 | A1 * | 9/2007 | Kopp | F23J 13/04 126/314 |
| 2007/0221201 | A1 * | 9/2007 | Kopp | F23J 13/00 126/314 |
| 2007/0227527 | A1 * | 10/2007 | Kopp | F23J 13/00 126/314 |
| 2007/0241242 | A1 * | 10/2007 | Kopp | F16L 3/137 248/74.5 |
| 2008/0257983 | A1 * | 10/2008 | Boys | F16B 2/08 239/276 |
| 2009/0024170 | A1 * | 1/2009 | Kirschman | A61B 17/8052 606/280 |
| 2010/0223764 | A1 * | 9/2010 | Prevot | F16L 23/08 24/279 |
| 2019/0022303 | A1 | 1/2019 | Headlee et al. | |

* cited by examiner

IV ORGANIZER

BACKGROUND

Health care providers can use a multitude of intravenous tubing with a single patient resulting in a convoluted mess of tubing. IV organizers have been proposed to help organize the mess of tubing, but such organizers can be overly expensive and can drive-up the cost of health care.

BRIEF DESCRIPTION OF THE DRAWINGS

Features and advantages of the invention will be apparent from the detailed description which follows, taken in conjunction with the accompanying drawings, which together illustrate, by way of example, features of the invention; and, wherein.

Figure 1:
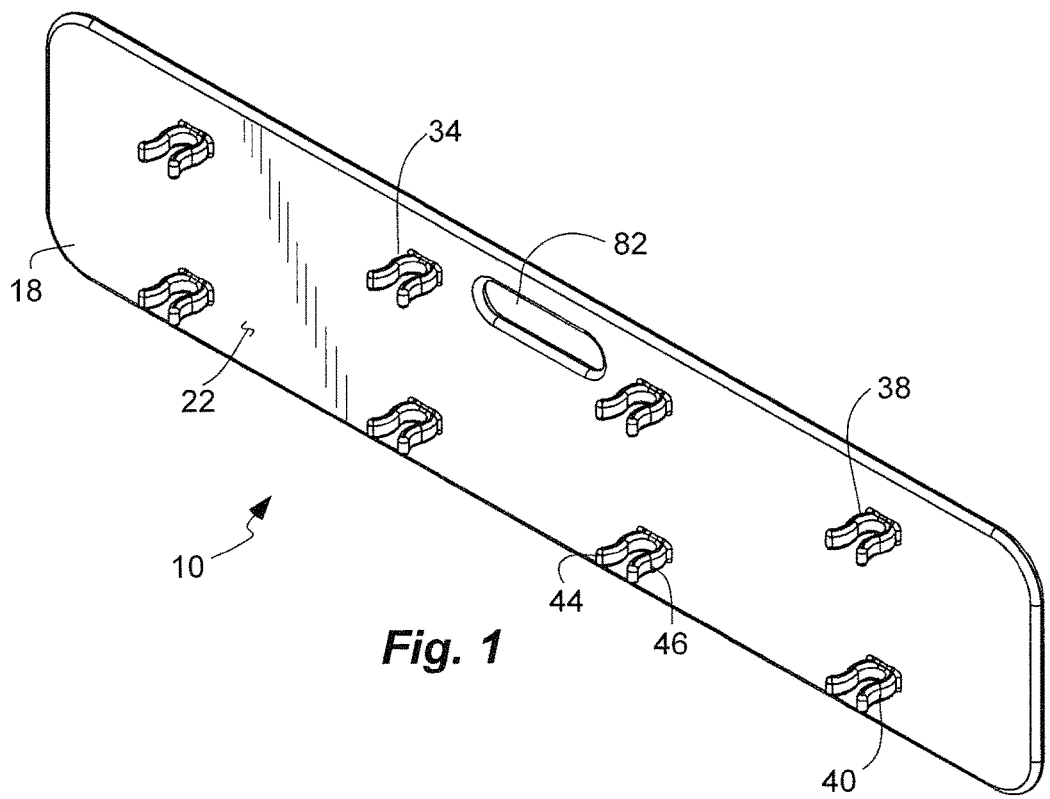
FIG. 1 is a perspective view of an IV organizer in accordance with an embodiment of the invention.
Figure 2:
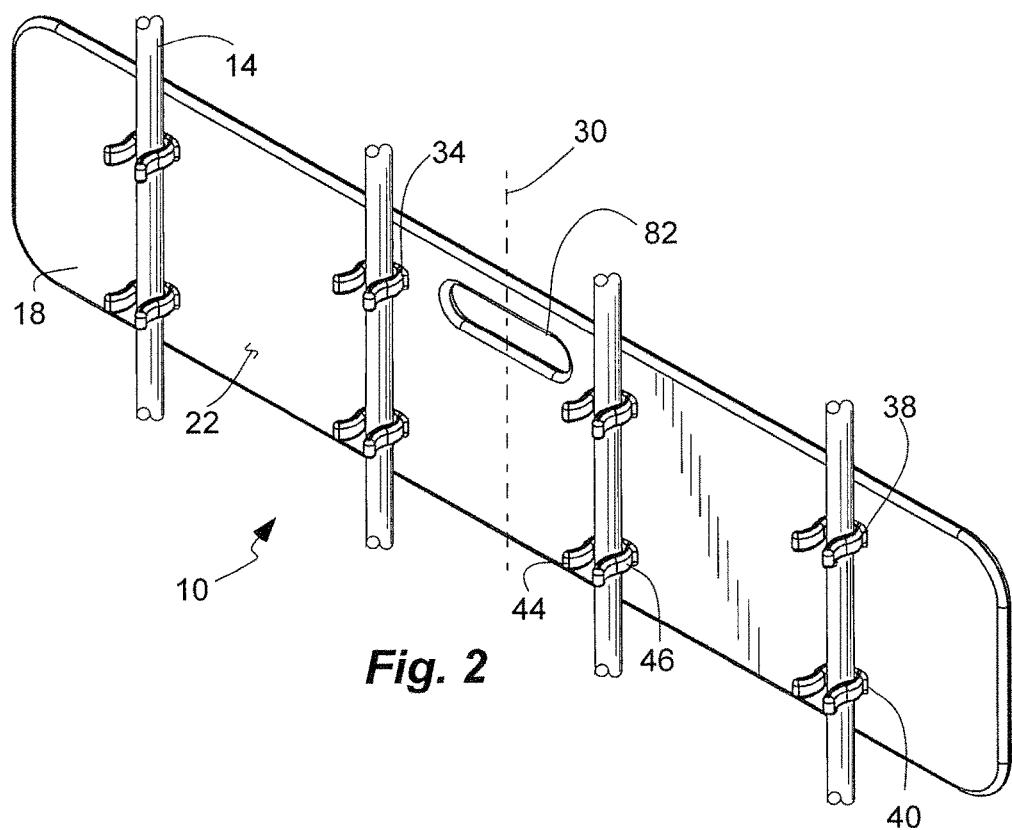
FIG. 2 is a perspective view of the IV organizer of FIG. 1, showing the IV organizer with intravenous tubing.
Figure 3:
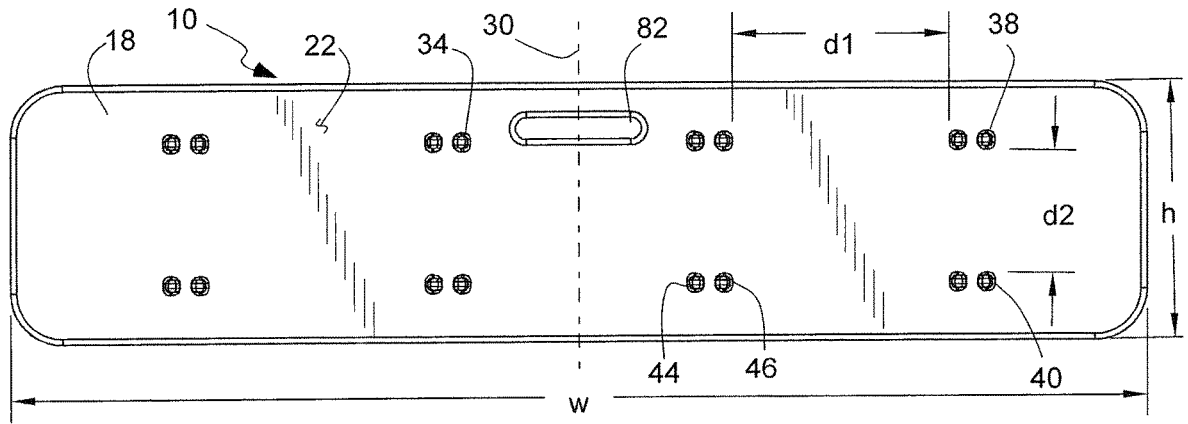
FIG. 3 is a front view of the IV organizer of FIG. 1.
Figure 4:
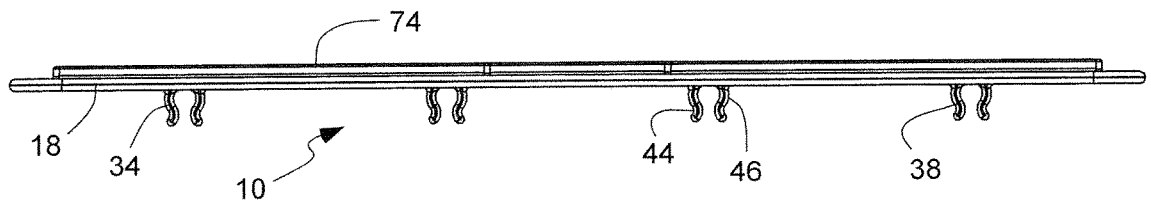
FIG. 4 is a top view of the IV organizer of FIG. 1.
Figure 5:
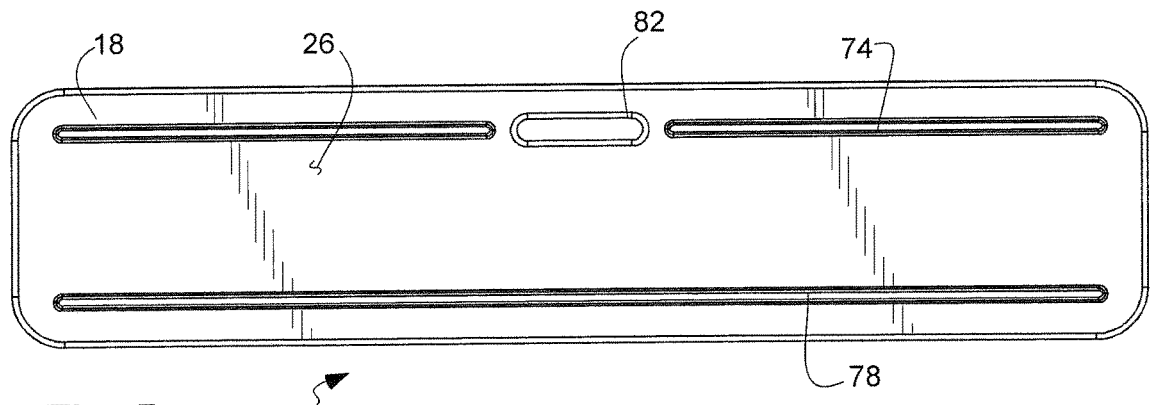
FIG. 5 is a rear view of the IV organizer of FIG. 1.
Figure 6:
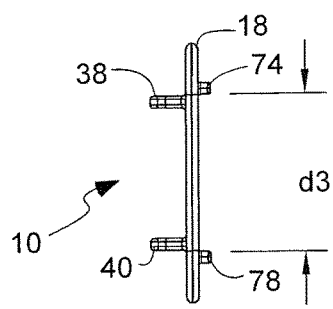
FIG. 6 is a side view of the IV organizer of FIG. 1.
Figure 7:
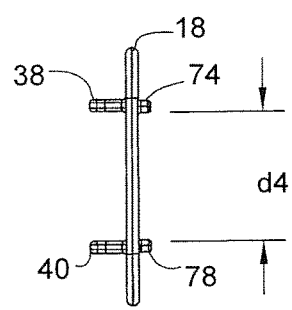
FIG. 7 is a side view of another IV organizer in accordance with an embodiment of the invention.
Figure 8:
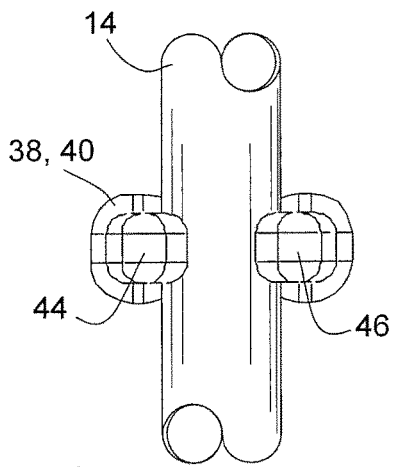
FIG. 8 is a schematic partial front view of the IV organizer of FIG. 1, showing the IV organizer with intravenous tubing.
Figure 11:
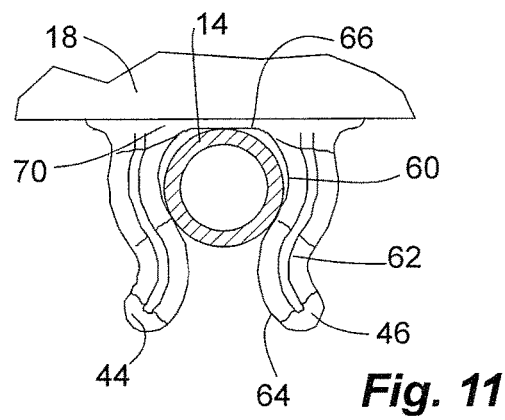
FIG. 11 is a schematic partial top view of another IV organizer in accordance with an embodiment of the invention.
Figure 9:
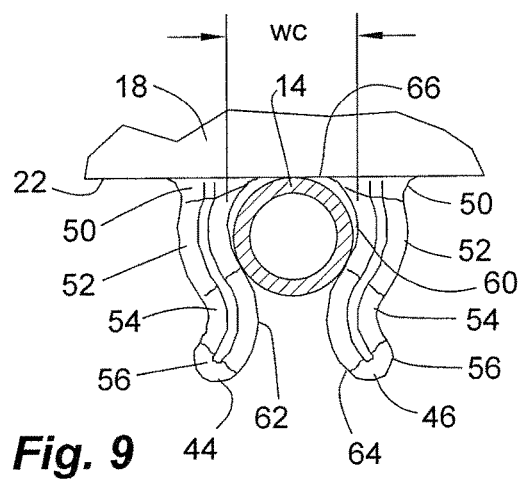
FIG. 9 is a schematic partial top view of the IV organizer of FIG. 1, showing the IV organizer with intravenous tubing.

Reference will now be made to the exemplary embodiments illustrated, and specific language will be used herein to describe the same. It will nevertheless be understood that no limitation of the scope of the invention is thereby intended.

DETAILED DESCRIPTION

Although the following detailed description contains many specifics for the purpose of illustration, a person of ordinary skill in the art will appreciate that many variations and alterations to the following details can be made and are considered to be included herein.

Accordingly, the following embodiments are set forth without any loss of generality to, and without imposing limitations upon, any claims set forth. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term in the specification, like "comprising" or "including," it is understood that direct support should be afforded also to "consisting essentially of" language as well as "consisting of" language as if stated explicitly and vice versa.

"The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein.

As used herein, "enhanced," "improved," "performance-enhanced," "upgraded," and the like, when used in connection with the description of a device or process, refers to a characteristic of the device or process that provides measurably better form or function as compared to previously known devices or processes. This applies both to the form and function of individual components in a device or process, as well as to such devices or processes as a whole.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

As used herein, "adjacent" refers to the relative placement of one object with respect to another object. In some examples, objects that are described as being "adjacent" to one another may be in a side-by-side or other similar positional relationship that can include objects that are in direct contact with one another and objects that are in close proximity to one another. The exact degree of proximity may in some cases depend on the specific context.

As used herein, "coupled" refers to a relationship of connection or attachment between one item and another item, and includes relationships of either direct or indirect connection or attachment. Any number of items can be coupled, such as materials, components, structures, layers, devices, objects, etc.

As used herein, "directly coupled" refers to a relationship of physical connection or attachment between one item and another item, where the items have at least one point of direct physical contact.

As used herein, "indirectly coupled" refers to a relationship of connection or attachment between one item and another item where the items do not have a point of direct physical contact with one another. Rather, such items can be connected, attached, or joined together by an intermediate item. For example, when a first layer of material is bound or joined to a second layer of material using an intermediate layer in between the first and second layer, the first and second layers can be said to be indirectly coupled.

Unless otherwise specified, the terms "IV tube" and "intravenous tubing" are used interchangeably herein. Intravenous tubing or IV tugging can be used to connect a bag of medication to a patient. Such tubing can have a diameter between 3-4 mm. Unless otherwise specified, the terms "IV tube" and "intravenous tubing" are used broadly to include catheters or catheter tubing. Catheter tubing can have a diameter between 3-5 mm.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

An initial overview of technology embodiments is provided below and then specific technology embodiments are described in further detail later. This initial summary is intended to aid readers in understanding the technology more quickly but is not intended to identify key features or essential features of the technology nor is it intended to limit the scope of the claimed subject matter.

An IV organizer is presented that can selectively receive and retain one or more intravenous tubes used by health care providers. The IV organizer can have multiple tubing clamps in a desired position and orientation to retain the IV tubes in the desired position and orientation. The IV organizer, alone or with multiple IV organizers, can secure IV tubes with respect to one another and the surrounding environment for safety and ease of use. In addition, the IV organizer can be formed of a recyclable material, and can comprise recycled material from previously used IV organizers. Thus, the IV organizer can be part of a system to collect and reuse used IV organizers.

Referring to FIGS. 1-11, one example of an IV organizer 10 is shown to selectively receive and retain intravenous tubing or IV tubes 14. The IV organizer 10 comprises a plate 18 that is substantially planar. In one aspect the plate 18 and the IV organizer 10 can be sized to accommodate four IV tubes 14. Thus, the plate 18 can have a size of approximately 6.5 inches by 1.5 inches. The plate 18 has a flat forward face 22, a rear face 26 (FIG. 5) opposite the forward face, a height h, a width w greater than the height h, and a longitudinal axis 30 defined by or aligned with the height h. The plate 18 can be wider than its height to accommodate multiple IV tubes 14.

An array of IV tube receivers 34 is located on the forward face 22 of the plate 22. The IV tube receivers 34 are spaced-apart laterally across the width w of the plate 18. The IV tubing receivers 34, and thus the IV tubes 14, can be spaced-apart sufficiently to allow handling, such as to accommodate fingers when securing and removing IV tubes 14. The IV tube receivers 34 can be spaced-apart by a distance d1 of approximately 1-2 inches, in one aspect, and 1.5 inches in another aspect. Each tube receiver 34 comprises a pair of clamps, such as an upper clamp 38 and a lower clamp 40. The pair of clamps, and the upper and lower clamps 38 and 40, are spaced-apart from one another longitudinally and aligned with respect to the longitudinal axis 30. The clamps 38 and 40 can be aligned so that they are associated together during use and to avoid confusion. The clamps 38 and 40 can be spaced-apart sufficiently to resist twisting or pivoting of the IV tubes 14 with respect to the plate 18. The upper and lower clamps 38 and 40 can be spaced-apart by a distance d2 of approximately 1-0.5 inches in one aspect, and 1 inch in another aspect. Thus, the IV tube receivers 38 can be spaced-apart from one another laterally by a distance d1 greater than a distance d2 longitudinally between the pair of clamps 38 and 40 of each tube receiver 38. In one aspect, the upper clamps 38 can be laterally aligned with one another, and the lower clamps 40 can be laterally aligned with one another, for support, as described below. In another aspect, the IV tube receivers 34, and thus the upper and lower clamps 38 and 40, can be longitudinally off-set with respect to an adjacent receiver to distinguish therebetween during use.

Each clamp 38 and 40 comprises a pair of fingers 44 and 46 extending from the forward face 22 of the plate 18. Each finger 44 and 46 can be serpentine with an S-shaped profile. The fingers 44 and 46 of each clamp 38 and 40 can be oriented opposite one another. Thus, the pair of fingers 44 and 46 in the clamp 38 and 40 can have a proximal end 50 located nearer to one another, a first intermediate portion 52 located farther from one another, a second intermediate portion 54 located nearer one another, and a free distal end 56 located farther from one another. Thus, fingers 44 and 46 define in the clamp 38 or 40 a wider channel 60 closer to the plate 18 to hold an IV tube 14, a narrower neck 62 adjacent to the wider channel 60 to restrain the IV tube 14 from leaving the wider channel, and a wider opening 64 adjacent to the narrower neck 62 to receive the IV tube.

The fingers 44 and 46 can be flexible and resilient. The fingers 44 and 46 can be flexible to separate upon receiving the IV tube 14 through the opening 64 and the neck 62 and into the channel 60, and resilient to return and grip the IV tube 14 in the channel 60 and to resist removal of the IV tube 14 from the channel 60. Thus, the flexible fingers 44 and 46 can resist pinching or compressing the IV tube 14. Similarly, the fingers can separate upon removal of the IV tube 14 from the channel 60, and through the neck 62, to the opening 64. In one aspect, the channel 60 can be sized to match the diameter of the IV tube 14. In another aspect, the channel 60 can be sized slightly smaller than the diameter of the IV tube 14 to grip the IV tube 14 and resist sliding of the IV tube 14 in the channel 60. The upper and lower clamps 38 and 40 of the pair of clamps can be spaced-apart from one another a distance d2 greater than a width we of the wider channel 60, that thus greater than the diameter of the IV tube 14.

In one aspect, a bottom 66 of the wider channel 60 can be flush with the forward surface 22 of the plate 18. Thus, the IV tubes 14 can be held against or abutting to the plate 18 for stability. In another aspect, referring to FIG. 11, each clamp 38 and 40 can have a base 70 between the plate 18 and the pair of fingers 44 and 46 to define a bottom 66 of the wider channel 60 of the clamp 38 or 40 that is raised with respect to the forward face 22. Thus, the IV tubes 14 can be separated the forward face 22 to aid visibility.

A pair of lateral rails or ribs, such as an upper rail 74 and a lower rail 78, extend from the rear face 26 of the plate 18. The pair of rails 74 and 78 extend perpendicularly to the longitudinal axis 30, and parallel with respect to one another. The rails 74 and 78 can be substantially aligned opposite the upper and lower clamps 38 and 40, respectively. The upper rail 74 can be substantially aligned opposite the upper clamps 38, and the lower rail 78 can be substantially aligned opposite the lower clamps 40. In one aspect, referring to FIG. 6, the pair of rails 74 and 78 can be spaced-apart a distance d3 greater than the distance d2 between the upper and lower clamps 38 and 40. In another aspect, referring to FIG. 7, the pair of rails 74 and 78 can be spaced-apart a distance d4 substantially equal the distance d2 between the upper and lower clamps 38 and 40. Thus, the rails 74 and 78 correspond to the clamps 38 and 40 and strengthen the clamps as force is applied to insert the IV tubes 14.

In addition, the plat 18 can have an aperture 82 therein to suspend the plate 18 from equipment.

Figure 13:
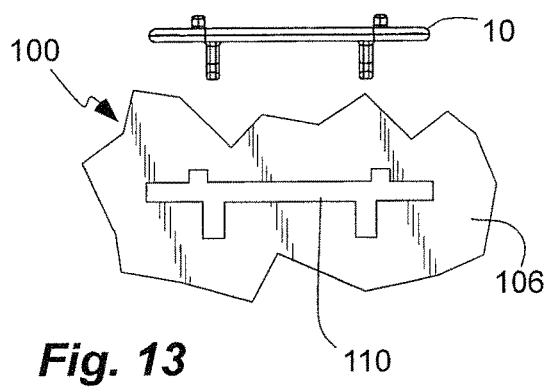
FIG. 13 is a schematic top view of the dedicated container of FIG. 12.
Figure 10:
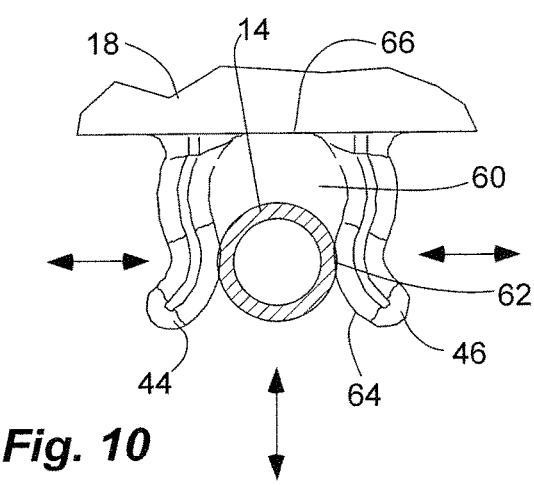
FIG. 10 is a schematic partial top view of the IV organizer of FIG. 1, showing intravenous tubing being secured and removed.
Figure 12:
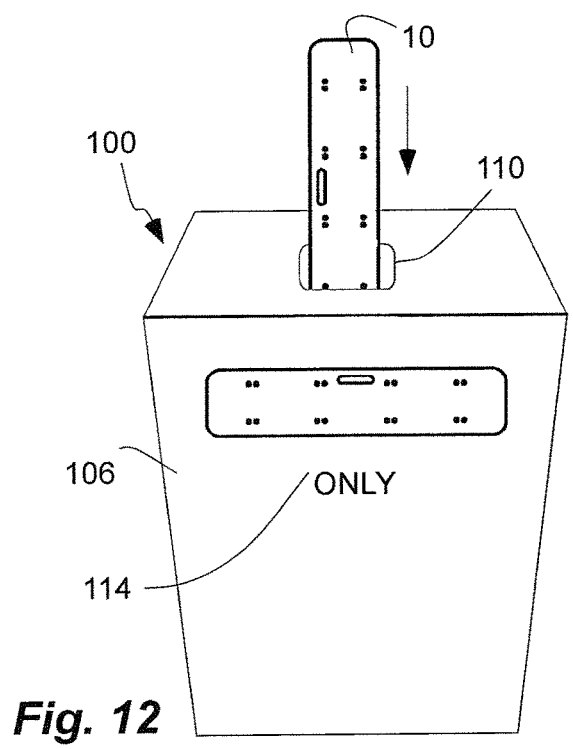
FIG. 12 is a schematic front view of a dedicated container in accordance with an embodiment to receive the used IV organizers of FIG. 1.

In one aspect, the IV organizer 10 can be formed of plastic, and can be formed by injection molding. In another aspect, the IV organizer 10 is formed of a polypropylene material comprising recycled material from previously used IV organizers. Thus, referring to FIGS. 12 and 13, the IV organizer 10 can be part of an IV system 100 with a dedicated recycling container 106 to receive the IV organizer 10 subsequent to use. The container 106 can have an opening 110 matching and shaped similar to, but slightly larger than, a lateral profile of the IV organizer 10. Thus, the opening 110 and the IV organizer 10 can be keyed to one another to accept only the IV organizer 10 and resist insertion of other objects. In addition, the container 106 can have indicium 114 indicative of the container's use, and/or instructing to only insert the designated IV organizer 10.

A method for organizing a plurality of intravenous tubing 14, and for using the IV organizer 10 described above, includes positioning an IV organizer 10 having an array of clamps 34 on a plate 14 and backed by ribs 74 and 78 opposite and substantially aligned with the array of clamps 34, and upper and lower claims 38 and 40. An IV tube 14 is pressed through an opening 64 of a pair of fingers 44 and 46 of a first clamp 38 of a pair of clamps spaced-apart from one another with the pair of fingers 44 and 46 separating as the IV tube 14 is pressed through the opening and a narrower neck 62, and into the a wider channel 60 between the pair of fingers 44 and 46, and with the pair of fingers 44 and 46 returning to grip the IV tube 14 in the channel 60 and to resist removal of the IV tube 14 from the channel 60. The IV tube 14 is pressed through an opening 64 of a pair of fingers 44 and 46 of a second clamp 40 of the pair of clamps, as described above. Another IV tube 14 is pressed through an opening 64 of a pair of fingers 44 and 46 of a first clamp 38 of another pair of clamps spaced-apart from one another, as described above. The another IV tube 14 is pressed through an opening 64 of a pair of fingers 44 and 46 of a second clamp 40 of the another pair of clamps, as described above. The IV tubes 14 are pulled through the necks 62 of the pairs of fingers 44 and 46 of the first and second clamps 38 and 40 of the pair of clamps and the another pair of claims with the pair of fingers 44 and 46 separating as the IV tube 14 is pulled through the narrower necks 62 and the openings 64. The IV organizer 10 is disposed of after use. In one aspect, the IV organizer 10 is disposed in a dedicated recycling container 106.

A method for providing IV organizers 10 as described above for organizing a plurality of intravenous tubing 14 includes making IV organizers 10 having an array of clamps 34 on a plate 18 and backed by ribs 74 and 78 opposite the array of clamps. In one aspect, the IV organizers 10 can be made of a material comprising polypropylene. The IV organizers 10 are distributed to health care providers. The IV organizers 10 are collected after use, defining used IV organizers. The used IV organizers 10 are destroyed and reduced to granular material. New IV organizers 10 are made with the granular material of the used IV organizers. In one aspect, the method can further include distributing dedicated recycling containers 106 to health care providers to receive the used IV organizers. The used IV organizers 10 can be collected from the dedicated recycling containers 106.

It is to be understood that the examples set forth herein are not limited to the particular structures, process steps, or materials disclosed, but are extended to equivalents thereof as would be recognized by those ordinarily skilled in the relevant arts. It should also be understood that terminology employed herein is used for the purpose of describing particular examples only and is not intended to be limiting.

Furthermore, the described features, structures, or characteristics may be combined in any suitable manner in one or more examples. In the description, numerous specific details are provided, such as examples of lengths, widths, shapes, etc., to provide a thorough understanding of the technology being described. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the foregoing examples are illustrative of the principles of the invention in one or more particular applications, it will be apparent to those of ordinary skill in the art that numerous modifications in form, usage and details of implementation can be made without the exercise of inventive faculty, and without departing from the principles and concepts described herein. Accordingly, it is not intended that the invention be limited, except as by the claims set forth below.

What is claimed is:

1. An IV organizer configured to selectively receive and retain intravenous tubing, the IV organizer comprising:
   a plate being planar and having a flat forward face, a rear face opposite the forward face, a height, a width greater than the height, and a longitudinal axis defined by the height;
   an array of IV tube receivers on the forward face of the plate and spaced-apart laterally across the width of the plate;
   each IV tube receiver comprising a pair of clamps spaced-apart from one another longitudinally and aligned with respect to the longitudinal axis, each pair of clamps configured to selectively receive and retain an IV tube;

the IV tube receivers being laterally spaced-apart from proximate IV tube receivers by a distance greater than a distance longitudinally between the pair of clamps of each IV tube receiver;

each of the pair of clamps having an upper clamp and a lower clamp, with the upper clamps laterally aligned with one another and with the lower clamps laterally aligned with one another;

each clamp comprising a pair of fingers extending from the forward face of the plate;

each finger being serpentine with an S-shaped profile;

the pair of fingers in each clamp having a proximal end located nearer to one another, a first intermediate portion located farther from one another, a second intermediate portion located nearer one another, and a free distal end located farther from one another, to define in the clamp a wider channel closer to the plate configured to hold an IV tube, a narrower neck adjacent to the wider channel configured to restrain the IV tube from leaving the wider channel, and a wider opening adjacent to the narrower neck configured to receive the IV tube;

the upper and lower clamps of the pair of clamps being spaced-apart from one another a distance greater than a width of the wider channel;

the fingers being flexible to separate upon receiving the IV tube through the opening and the neck and into the channel, and resilient to return and grip the tube in the channel and to resist removal of the IV tube from the channel;

a pair of lateral rails on the rear face of the plate, the pair of rails extending perpendicularly to the longitudinal axis, the pair of rails being positioned inside and spaced-apart from a perimeter of the plate;

the pair of lateral rails having an upper rail backing and aligned opposite the upper clamps, and a lower rail backing and aligned opposite the lower clamps;

an aperture in the plate configured to suspend the plate; and the IV organizer being formed of a polypropylene material comprising recycled material from previously used IV organizers.

2. The IV organizer of claim 1, further in combination with:
a dedicated recycling container configured to receive the IV organizer subsequent to use.

3. An IV organizer configured to selectively receive and retain intravenous tubing, the IV organizer comprising:
a plate being planar and having a flat forward face, a rear face opposite the forward face, a height, a width greater than the height, and a longitudinal axis defined by the height;

an array of IV tube receivers on the forward face of the plate and spaced-apart across the width of the plate;

each IV tube receiver comprising a pair of clamps spaced-apart from one another and aligned with respect to the longitudinal axis;

the IV tube receivers being laterally spaced-apart from proximate IV tube receivers by a distance greater than a distance longitudinally between the pair of clamps of each IV tube receiver;

each of the pair of clamps having an upper clamp and a lower clamp, with the upper clamps laterally aligned with one another and with the lower clamps laterally aligned with one another;

each clamp comprising a pair of fingers extending from the forward face of the plate;

a pair of lateral rails on the rear face of the plate, the pair of rails extending perpendicularly to the longitudinal axis, the pair of rails being positioned inside and spaced-apart from a perimeter of the plate; and the pair of lateral rails having an upper rail backing and aligned opposite the upper clamps, and a lower rail backing and aligned opposite the lower clamps.

4. The IV organizer of claim 3, further comprising:
each finger being serpentine with an S-shaped profile;

the pair of fingers in each clamp having a proximal end located closer to one another, a first intermediate portion located farther from one another, a second intermediate portion located nearer one another, and a free distal end located farther from one another, to define in the clamp a wider channel closer to the plate configured to hold an IV tube, a narrower neck adjacent to the wider channel configured to restrain the IV tube, and a wider opening adjacent to the narrower neck configured to receive the IV tube; and the fingers being flexible to separate upon receiving the IV tube through the opening and the neck and into the channel, and resilient to return and grip the tube in the channel and to resist removal of the IV tube from the channel.

5. The IV organizer of claim 4, wherein the upper and lower clamps of the pair of clamps are spaced-apart from one another a distance greater than a width of the wider channel.

6. The IV organizer of claim 3, wherein the tube receivers are laterally spaced-apart from proximate tube receivers by a distance greater than a distance between the pair of clamps of each tube receiver.

7. The IV organizer of claim 4, wherein a bottom of the wider channel of the clamp is flush with respect to the forward face.

8. The IV organizer of claim 4, wherein each clamp has a base between the plate and the pair of fingers to define a bottom of the wider channel of the clamp raised with respect to the forward face.

9. The IV organizer of claim 3, wherein the IV organizer is formed of a polypropylene material comprising recycled material from previously used IV organizers.

10. The IV organizer of claim 3, further comprising:
an aperture in the plate configured to suspend the plate.

11. An IV organizer configured to selectively receive and retain intravenous tubing, the IV organizer comprising:
a plate being planar and having a flat forward face, a rear face opposite the forward face, a height, a width greater than the height, and a longitudinal axis defined by the height;

an array of IV tube receivers on the forward face of the plate and spaced-apart across the width of the plate;

each IV tube receiver comprising a pair of clamps spaced-apart from one another and aligned with respect to the longitudinal axis;

the IV tube receivers being laterally spaced-apart from proximate IV tube receivers by a distance greater than a distance longitudinally between the pair of clamps of each IV tube receiver;

each of the pair of clamps having an upper clamp and a lower clamp, with the upper clamps laterally aligned with one another and with the lower clamps laterally aligned with one another;

each clamp comprising a pair of fingers extending from the forward face of the plate;

a pair of lateral rails on the rear face of the plate, the pair of rails extending perpendicularly to the longitudinal axis, the pair of rails being positioned inside and spaced-apart from a perimeter of the plate; and the pair of lateral rails having an upper rail backing and aligned opposite the upper clamps, and a lower rail backing and aligned opposite the lower clamps.

12. The IV organizer of claim 11, further comprising:
each finger being serpentine with an S-shaped profile;
the pair of fingers in each clamp having a proximal end located closer to one another, a first intermediate portion located farther from one another, a second intermediate portion located nearer one another, and a free distal end located farther from one another, to define in the clamp a wider channel closer to the plate configured to hold an IV tube, a narrower neck adjacent to the wider channel configured to restrain the IV tube, and a wider opening adjacent to the narrower neck configured to receive the IV tube; and
the fingers being flexible to separate upon receiving the IV tube through the opening and the neck and into the channel, and resilient to return and grip the tube in the channel and to resist removal of the IV tube from the channel.

13. The IV organizer of claim 12, wherein the upper and lower clamps of the pair of clamps are spaced-apart from one another a distance greater than a width of the wider channel.

14. The IV organizer of claim 12, wherein a bottom of the wider channel of the clamp is flush with respect to the forward face.

15. The IV organizer of claim 12, wherein each clamp has a base between the plate and the pair of fingers to define a bottom of the wider channel of the clamp raised with respect to the forward face.

16. The IV organizer of claim 11, wherein the IV organizer is formed of a polypropylene material comprising recycled material from previously used IV organizers.

17. The IV organizer of claim 11, further comprising:
an aperture in the plate configured to suspend the plate.

18. The IV organizer of claim 11 in combination with a dedicated recycling container configured to receive the IV organizer subsequent to use; and, the dedicated recycling container comprising:
an opening in the container matching a lateral profile of the IV organizer.

19. The IV organizer of claim 3 in combination with a dedicated recycling container configured to receive the IV organizer subsequent to use; and, the dedicated recycling container comprising:
an opening in the container matching a lateral profile of the IV organizer.

20. The IV combination of claim 2, further comprising:
an opening in the container matching a lateral profile of the IV organizer.

* * * * *